United States Patent [19]

Shashoua et al.

[11] Patent Number: 5,284,876
[45] Date of Patent: Feb. 8, 1994

[54] METHOD OF TREATING TARDIVE DYSKINESIA USING DOPAMINERGIC AGENTS OF PRODRUGS OF THERAPEUTIC AGENTS

[75] Inventors: Victor E. Shashoua, Brookline; Gary W. Hesse, Winchester, both of Mass.

[73] Assignee: Neuromedica, Inc., Cambridge, Mass.

[21] Appl. No.: 897,563

[22] Filed: Jun. 11, 1992

Related U.S. Application Data

[63] Continuation of Ser. No. 564,046, Aug. 7, 1990, abandoned, which is a continuation-in-part of Ser. No. 535,812, Jun. 11, 1990, abandoned, which is a continuation-in-part of Ser. No. 315,134, Feb. 24, 1989, Pat No. 4,933,324, which is a continuation-in-part of Ser. No. 160,667, Feb. 26, 1988, Pat. No. 4,939,174.

[51] Int. Cl.$^5$ .................... A61K 31/165; A61K 37/02
[52] U.S. Cl. ........................... 514/549; 514/17; 514/772.6; 514/549; 514/400
[58] Field of Search ............... 514/549, 78, 649, 219, 514/220, 222

[56] References Cited

U.S. PATENT DOCUMENTS

| | | | |
|---|---|---|---|
| 4,346,085 | 8/1982 | Growdon et al. | 424/199 |
| 4,351,831 | 9/1982 | Growdon et al. | 421/199 |
| 4,550,109 | 10/1985 | Folkers et al. | 514/249 |
| 4,554,272 | 11/1985 | Bock et al. | 541/219 |
| 4,636,494 | 1/1987 | Growdon et al. | 541/78 |
| 4,684,646 | 8/1987 | Chang et al. | 541/221 |
| 4,933,324 | 6/1990 | Shashoua | 514/549 |
| 4,939,174 | 7/1990 | Shashoua | 514/549 |

FOREIGN PATENT DOCUMENTS

| | | |
|---|---|---|
| 30009 | 6/1981 | European Pat. Off. . |
| 91694 | 10/1983 | European Pat. Off. . |
| 8500520 | 2/1985 | PCT Int'l Appl. . |

OTHER PUBLICATIONS

T. Higuchi et al., "Prodrugs as Novel Drug Delivery Systems", American Chem. Society, ACS Symposium Series, vol. 14, pp. 14–15 (1975).
S. Iwakami et al., "Inhibition of Arachidonate 5-Lipoxygenase by Phenolic Compounds", Chem. Pharm. Bull. (Japan), 34(9), 3960–3963, 1986.
Y. Makino et al., Chemical Abstracts, vol. 106, No. 12, issued Mar. 23, 1987, "Pharmaceuticals Permeable to Blood-Brain Barrier".
G. Dhopeshwarker, Chemical Abstracts, vol. 76, No. 16, issued Apr. 17, 1972, "Fatty Acid Transport into the Brain".
R. Specter, Chemical Abstracts, vol. 108, No. 11, issued Mar. 14, 1988, "Fatty Acid Transport Through the Blood-Brain Barrier".
I. Yamatsu et al., Chemical Abstracts, vol. 100, No. 19, issued May 7, 1984, "Polyprenyl Carboxylic Acid Amides".
V. E. Shashoua, et al., "γ-Aminobutyric Acid Esters.1. Synthesis . . . ", Journal of Medicinal Chemistry, vol. 27, No. 5, pp. 659–664 (1984).
J. N. Jacob, et al,, "γ-Aminobutyric Acid Esters.2. Synthesis Brain Uptake . . . ", J. of Medicinal Chemistry, vol. 28, No. 1, pp. 106–110 (1985).
G. W. Hesse et al., "Inhibitory Effect of Cholesteryl γ-Aminobutyrate" Neurolpharmacology, vol. 24, No. 2, pp. 139–146 (1985).
K. A. Jacobson et al., "Adenosine analogs with covalently attached lipids . . . ", FEBS Letters, vol. 225, Nos. 1, 2 pp. 97–102 (Dec. 1987).

(List continued on next page.)

Primary Examiner—Frederick E. Waddell
Assistant Examiner—T. J. Criares
Attorney, Agent, or Firm—Wolf, Greenfield & Sacks

[57] ABSTRACT

This invention pertains to a method for treating a subject for Tardive Dyskinesia by administering a dopaminergic agent to the subject such that the dopaminergic agent enters the brain or by administering a prodrug of a therapeutic agent. The dopaminergic agent preferably is 2 prodrug formed by coupling dopamine to a fatty acid. This invention further pertains to methods of providing pharmaceutical preparations and packaged pharmaceuticals for Tardive Dyskinesia.

23 Claims, 3 Drawing Sheets

OTHER PUBLICATIONS

A. Garzon-Aburbeh et al., "A Lymphotropic Prodrug of L-Dopa:Synthesis" J. Med. Chem. 29: 687–691 (1986).

U. K. Mazumdar & D. C. Dey, "Preparation and Evaluation of Ethambutol Derivatives", Indian J. Pharm. Sci. 47(6): 179–180 (1985).

R. J. Baldessarini et al., "Dopamine and the Pathophysiology of Dyskinesis . . .", Ann. Rev. Neurosci. 3: 23–41 (1980).

J. P. Lohr et al., "Neuroleptic-Induced Movement Disorders . . .", Psychiatry, vol. 3, (1989), J. B. Lippincott Co., Phila., Pa., ed. R. Michels.

J. N. Jacob et al., "Gamma-aminobutyris Acid Esters . . .", J. Med. Chem. 30:1573–1576 (1987).

G. W. Hesse et al., "Uptake in Brain and Neurophysiological . . .", Neuropharmacol. 27:637–640 (1988).

J. N. Jacob et al., "Synthesis, Brain Uptake and Pharmacological . . .", J. Med. Chem. 33:733–736 (1990).

METHOD OF TREATING TARDIVE DYSKINESIA USING DOPAMINERGIC AGENTS OF PRODRUGS OF THERAPEUTIC AGENTS

This application is a continuation application of Ser. No. 07/564,046 filed Aug. 7, 1990, now abandoned, which is a continuation-in-part of Ser. No. 07/535,812 filed Jun. 11, 1990, now abandoned, which is a continuation application of Ser. No. 07/315,134 filed Feb. 24, 1989, now U.S. Pat. No. 4,933,324, which is a continuation-in-part of Ser. No. 07/160,667 filed Feb. 26, 1988, now U.S. Pat. No. 4,939,174.

BACKGROUND OF THE INVENTION

Tardive Dyskinesia (TD) is a neurological syndrome consisting of spontaneous and largely uncontrollable oral or facial movements (such as chewing, swallowing, lip smacking and tongue protrusion) and head/neck movements. Choreiform movements of the fingers and other extremities are also commonly observed (McDowell et al., *Clinical Neurology*, Chapter 38, 1988; Lohr et al., *Psychiatry*, Chapter 70, 1989).

The condition is an undesirable side effect associated with long-term or high dose therapy with neuroleptic drugs. The condition appears after several months or years of neuroleptic therapy and persists after discontinuation of the drug or drugs. Symptoms may persist indefinitely, but in some cases slow remission is observed over months or years. In general, the likelihood of remission is lower with longer exposure to neuroleptics and with increasing age of the patient (McDowell et al., *Clinical Biology*, Chapter 38, 1988).

Estimates of the incidence of TD vary from about 10% to over 40% of the patients exposed to neuroleptic drugs for one year or longer. All types of neuroleptics seem to be associated with the syndrome, as well as antiemetic agents with dopamine receptor blocking actions (Wiholm et al., *British Medical Journal*, Vol. 288, pp. 545-547, 1984). Older patients appear to be at somewhat higher risk than younger patients (Tepper et al., *Journal of Clinical Psychiatry*, Vol. 40, pp. 508-516, 1979; Baldessarini, *Journal of Clinical Psychiatry*, Vol. 46, pp. 8-13, 1985).

The exact biochemical basis of the syndrome is not well understood. The prevailing opinion is that TD symptoms are largely, but not entirely, explained as manifestations of overactive central nervous system (CNS) dopaminergic systems. Dopamine receptor supersensitivity resulting from chronic treatment with dopamine receptor blockers is cited as a plausible cause of the apparent hyperdopaminergic state (Lohr et al., *Psychiatry*, Chapter 70, 1989). Dopaminergic hyperactivity could also result from enhanced synthesis and/or storage of dopamine as an adaptation to chronic presynaptic dopamine receptor blockade (Baldessarini et al. *Annual Review of Neuroscience*, Vol. 3, pp. 23-41, 1980).

The pharmacological profile of TD indicates that agents which tend to directly or indirectly inhibit CNS dopaminergic systems generally tend to relieve TD symptoms, while compounds which enhance dopaminergic transmission exacerbate the symptoms (Baldessarini et al. *Annual Review of Neuroscience*, Vol. 3, pp. 23-41, 1980). In particular, low doses of apomorphine, bromocriptine and amine depleting agents such as reserpine tend to be helpful (Fahn. *Clinical Neuropharmacology*, Vol. 6, pp. 151-158, 1983; Thorner et al., *Bromocriptine: A Clinical and Pharmacological Review*, Raven Press, New York, pp. 139-140, 1980). However, such compounds often have toxic or other undesirable side effects and frequently have a narrow and variable effective dose range which makes prolonged use difficult or impractical.

There are many obstacles to developing treatments which require the delivery of a drug to an active site in the body. Ingestion of a drug often is not possible because many drugs will not survive the environment of the stomach. Thus, easy and safe self administration of many drugs is not available. A drug, of course, can be injected directly into the blood stream of a patient. However, frequent injections at great inconvenience to a patient may be necessary because some drugs do not survive for very long in the bloodstream. The inability of a drug to survive in the bloodstream can be overcome in certain instances by increasing the dosage o by increasing the frequency of administration. However, the dosage can result in undesirable side effects and increasing the frequency of administration only adds inconvenience.

The delivery of a neuroactive drug to the central nervous system (CNS) via the bloodstream involves an extraordinary obstacle; the drug must be capable of crossing the blood brain barrier. The blood brain barrier may loosely be regarded as a biological exclusion barrier involving both passive and active transport, which barrier controls the exchange of materials between the plasma and the central nervous system. Many drug substances are unable to pass through this barrier in efficacious amounts or at all.

SUMMARY OF THE INVENTION

This invention relates to a method for treating a subject for Tardive Dyskinesia comprising administering a pharmaceutically effective amount of a dopaminergic agent to the subject such that the dopaminergic agent enters the brain. In the preferred method for treating Tardive Dyskinesia a pharmaceutically effective amount of a prodrug preferably formed of a fatty acid coupled to the dopaminergic agent is administered to the subject.

The preferred method of the present invention uses prodrugs which are stable in the environment of both the stomach and the bloodstream and therefore can be administered orally. The prodrugs pass readily through the blood brain barrier delivering the dopaminergic agent to active sites in the brain. The preferred dopaminergic prodrugs have a brain penetration index of at least two times the brain penetration index of the dopaminergic agent alone. Further, upon entering the central nervous system, the prodrugs are hydrolyzed into the fatty acid and the dopaminergic agent. The fatty acid preferably is a normal component of the central nervous system and is inactive and harmless. The preferred dopaminergic agent is released in active form but should no result in toxic side effects because it is also a naturally occurring component of the brain.

The present invention also pertains to methods of providing a pharmaceutical preparation for Tardive Dyskinesia by forming the above described prodrugs and providing instructions for using the prodrug to treat Tardive Dyskinesia. The invention further pertains to a packaged pharmaceutical containing a prodrug and instructions for using the prodrug to treat Tardive Dyskinesia.

It is an object of the invention to provide a method for treating Tardive Dyskinesia that will not induce tolerance and will not cause harmful side effects.

Another object of the invention is to provide a carrier molecule capable of being combined with a dopaminergic agent to form a prodrug that will readily cross the blood brain barrier and allow release of the dopaminergic agent into the central nervous system.

Another object of the invention is to provide a prodrug that is stable in the environment of the stomach and in the bloodstream.

Another object of the invention is to provide an amide derivative of a dopaminergic agent with biological activity useful for treating Tardive Dyskinesia.

Yet another object of the invention is to provide a method for treating tardive dyskinesia.

DETAILED DESCRIPTION

Figure 1:
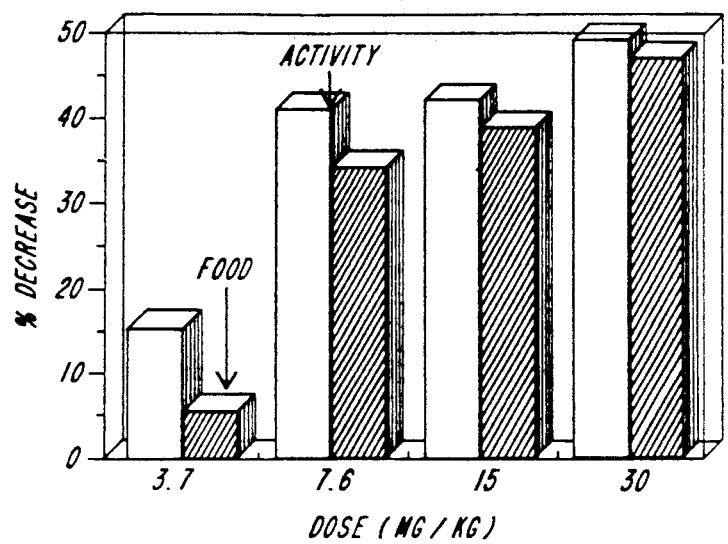
FIG. 1 is a graph showing the effect of the prodrug of the preferred embodiment on motor activity of mice.

The present invention relates to a method for treating a subject for Tardive Dyskinesia by administering a pharmaceutically effective amount of a dopaminergic agent to a subject such that the dopaminergic agent enters the brain. The dopaminergic agent is preferably administered as a prodrug comprising a fatty acid coupled to the dopaminergic agent.

The term subject is intended to include living organisms susceptible to Tardive Dyskinesia, e.g. mammals or birds. Examples of subjects include humans, dogs, cats, horses, and cows.

The term Tardive Dyskinesia is intended to include neurological syndromes consisting of spontaneous and largely uncontrollable oral or facial movements, such as chewing, swallowing, lip-smacking, tongue protrusion, lateral jaw movements, and head/neck movements, or uncontrollable movements of the fingers and other extremities. For example, such movements are a known side effect of prolonged or high dose therapy with antipsychotic or neuroleptic drugs. Withdrawal dyskinesia's and dystonias also are intended to be encompassed by the term Tardive Dyskinesia. Withdrawal dyskinesias develop during a reduction in dose of neuroleptic or antipsychotic drugs or shortly following the discontinuance of the drugs. Dystonias are disorders of the muscle tone. Tardive Dyskinesia like syndromes can also occur naturally without being caused by neuroleptic drugs. These naturally occurring syndromes also are intended to be encompassed by the term Tardive Dyskinesia.

The term dopaminergic agent is intended to encompass dopamine, derivatives of dopamine, compounds which have dopamine like actions on dopamine receptors, or combinations thereof. The dopaminergic agent is introduced in a manner such that it has specific dopaminergic properties that inhibit dopamine release and transmission in pathways involving Tardive Dyskinesia and preferably without substantial excitatory agonist properties. Dopamine derivatives are compounds which are structurally similar to dopamine. For example, dopamine derivatives can have one or both of the hydroxyl groups or the amino group chemically modified, e.g. blocked by esterification or can have substituents (e.g. lower alkyl groups) on the alkyl chain of the amino moiety. The derivatives would have to be capable of having a dopaminergic effect and following coupling to the carrier be capable of functioning in the same or similar manner as dopamine in its ability to significantly reduce or eliminate the symptoms associated with Tardive Dyskinesia. The dopaminergic agents useful in this invention are those which are non-toxic to the subject and do not produce undesirable side effects. Non-toxic is intended to include substantially non-toxic, e.g the agents may have a minimal level of toxicity which does not cause a significant harm to the subject. For purposes of this invention, the symbol D is intended to represent dopaminergic agent.

The term therapeutic agent is intended to encompass agents capable of eliminating or significantly reducing symptoms associated with Tardive Dyskinesia. The therapeutic agent can be a dopaminergic agent or can include agents not considered to be dopaminergic agents, e.g. bromocriptine.

The dopaminergic agent preferably is introduced into the subject in the form of a prodrug and the therapeutic agent is introduced into the subject in the form of a prodrug. For purposes of discussion below, the term agent is intended to encompass both therapeutic and dopaminergic agents. The prodrug can be formed by coupling the agent to a carrier which will facilitate delivery of the agent across the blood brain barrier. Types of carriers which can be used include fatty acids, glucose, inositol, 1-4-dihydropyridine, lipids, proteins and peptides. The proteins and peptides can be synthetic or naturally occurring. The term peptide is intended to include small proteins and particularly those molecules having on the order of about 100 amino acids or less. Examples of proteins useful as carriers include antibodies specific for receptors within the brain, albumin, insulin, or growth factors.

The preferred prodrug is formed from a fatty acid coupled to the agent, the fatty acid being capable of delivering the agent across the blood brain barrier. The fatty acid carrier preferably has between about 16 and about 26 carbon atoms, and more preferably between about 20 and about 24 carbon atoms. A preferred carrier is

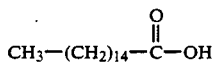

Most preferably, the carrier is the all cis form of 4, 7, 10, 13, 16, 19 docosahexa-enoic acid.

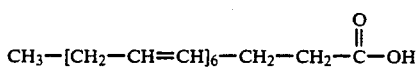

The length, the degree of saturation and whether the fatty acid is naturally occurring in the brain effects the ability of the fatty acid to serve as a carrier to deliver the agent across the blood brain barrier to an active site in the brain. Fatty acids which are partially unsaturated and occur naturally in the brain are particularly preferred as carriers. Fatty acids which occur naturally in the brain include those with 16 carbon atoms and 0, 1 or 2 double bonds (C16:0; C16:1; and C16:2), those with 18 carbon atoms and 1, 2 or 3 double bonds (C18:1; C18:2; and C18:3), those with 20 carbon atoms and 1, 2 or 4 double bonds (C20:1; C20:2; and C20:4) and those with 22 carbon atoms and 4, 5 or 6 double bonds (C22:4; C22:5; and C22:6). The position of the double bonds can be between any of the carbon atoms in the fatty acids, the preferred loci being those which occur naturally in the fatty acids of the central nervous system. The C16:0 and C22:6 are the preferred fatty acid carriers due to their preference for concentrating in the synaptosamal membranes, with C22:6 being most preferred. It also has been found that C18:3 acts above average in its ability to deliver a compound across the blood brain barrier.

Branched chain fatty acids having between 16 and 26 carbon atoms can also be used within the present invention. A hydrogen atom of the foregoing fatty acids can be replaced with a methyl, ethyl or isopropyl substituent at various positions along the carbon chain.

Other examples of carriers include the naturally occurring polyisoprenoids (dolicols) and analogues thereof such as

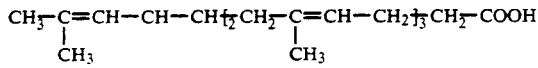

The agent can be coupled to the fatty acid via a group capable of being attached, directly or indirectly, to the hydroxyl group of the fatty acid. The hydroxyl group of the fatty acid can form, for example, an ester or amide bond with the agent. The hydroxyl or amino group of the agent can form a bond with the fatty acid. A variety of reactions can be used involving reacting the agent (or a protected derivative thereof) having one, free hydroxyl or amino group with the corresponding fatty acid carrier or an activated derivative thereof. A free hydroxyl group can form an ester bond with the fatty acid or activated derivative thereof and the free amino group can form an amide bond with the fatty acid or activated derivative thereof.

An agent having its two hydroxyl groups protected by a protecting group, e.g. acetonide, can be reacted with the fatty acid carrier in the presence of a water removing compound (e.g. dicyclohexyl carbodiimide) forming an amide. The reaction is usually conducted in the presence of the solvent such as dioxane, tetrahydrofurane, N-methylpyrrolidone or dimethylforamide at ambient temperature. The solvent can be removed and the desired product can be extracted using a suitable solvent such as methylene chloride. Protecting groups can be removed by treating with a suitable acid, e.g. 4N HCl in dioxane. The amino group of the agent can also be coupled to the carboxyl group of the carrier by using an acid chloride or a low carbon ester derivative of the carrier and forming amide bonds by liberating HCl or an alcohol respectively.

The hydroxyl groups, alternatively, can be coupled to the fatty acid carrier via ester bonds using techniques similar to those described above (e.g. using the anhydride derivative, the acid chloride derivative, or the free acid form of the carrier). Alternatively, a spacer molecule capable of linking the fatty acid to the agent can be used. Couplings such as phosphoramide, sulfate, sulfonate, phosphate or urethane can be used to couple the fatty acid to the dopaminergic agent as will be recognized by one of ordinary skill in the art.

The preferred bonds for coupling the fatty acid to the agent are those capable of surviving the environment of the stomach thereby allowing oral administration of the prodrug to the subject. The preferred bonds also should hydrolyze when in the brain. An example of such a bond is an amide bond. Bonds incapable of surviving the environment of the stomach, e.g. ester bond, may also be used to link the fatty acid to the agent. Prodrugs coupled with bonds such as these can be injected or protected from the environment of the stomach using coatings or liposomes, for example. Those skilled in the art would know how to coat such compounds for this purpose. Such a coating may be called for even in the presence of an amide bond between the carrier and the drug.

The agent or prodrug of the agent is administered to the subject in a pharmaceutically effective amount. A pharmaceutically effective amount is that amount which significantly reduces or eliminates the symptoms associated with Tardive Dyskinesia. A pharmaceutically effective amount can be determined on an individual basis and will be based, at least in part, on consideration of the subjects' size, the severity of symptoms to be treated, the results sought, and the specific fatty acid used as the carrier. Thus, a pharmaceutically effective amount can be determined by one of ordinary skill in the art employing such factors and using no more than routine experimentation. For treating Tardive Dyskinesia with dopaminergic or therapeutic agent prodrugs, amounts in the range of about 10-20,000 micrograms per kilogram of body weight are preferred.

Administration can be made by a method which allows the dopaminergic agent to reach the bloodstream and penetrate the blood brain barrier. The agent or prodrug thereof can be administered orally, by subcutaneous or other injection, intravenously, intramuscularly, parenternally, transdermally or rectally.

The form in which the agent or prodrug thereof is administered will depend on the route by which it is administered. For example, when the agent or prodrug thereof is administered orally, dragees, tablets, syrups, capsules or ampules can be used. A suppository can be used when rectal administration is the chosen route, or a pomade or a gel can be used for transdermal administration. Solutions or emulsions are alternative forms for administration.

Slow release capsules and other protective means are suitable for the oral administration of the prodrugs of the invention due to the protection afforded against hydrolysis in the gastrointestinal track. Preferred are those capsules which permit the prodrugs to bypass the stomach.

The agents or prodrugs of the invention can be prepared in pharmaceutical preparations or doses containing the agents themselves and a pharmaceutically acceptable carrier. A pharmaceutically acceptable carrier is a carrier capable of being co-administered with the agent or prodrug and not adversely affecting the dopaminergic or therapeutic activity of the agent or delivery of the agent across the blood brain barrier. The carrier can be solid or liquid. Examples of liquid carriers include water, an aqueous solution of non-toxic salts, such as sterile physiological solutions of saline, or aqueous solutions containing organic solvents, such as ethanol. Also suitable are emulsions, such as oil-in-water. Solid carrier include both nutritive carrier, such as sucrose or gelatin, and non-nutritive carriers, such as cellulose or talc.

PREFERRED EMBODIMENT

The most preferred embodiment of the invention is

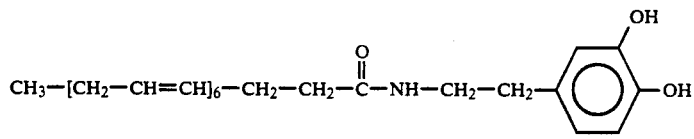

This compound has extraordinary and unexpected properties. This compound, hereinafter called compound 8739, is believed to be inactive until it crosses the blood brain barrier to release dopamine into the central nervous system (CNS) Unlike dopamine, compound 8739 survives sufficiently in the environment of the stomach and the bloodstream and therefore can be administered orally.

Compound 8739 has an enhanced ability to cross the blood brain barrier, with a brain penetration index (BPI) of about 33, as compared to about 4 for dopamine. It is believed to be inactive as a prodrug in that it does not bind to either D-1 or D-2 dopamine receptors. Rather, once in the central nervous system, dopamine is released as an active fragment of compound 8739. In addition, compound 8739 is taken up into the synaptosomal membranes preferentially, the synaptosomal membranes being the site of activity for the dopamine. This property may contribute to the compound's desirable properties. Compound 8739 has specific dopaminergic properties that inhibit dopamine release and transmission without substantial excitatory agonist properties.

Once dopamine is released as an active fragment, it produces effects on oral dyskinesia and on general locomotor activity in mice in a dose dependent manner. Oral dyskinesia decreased by as much as 44% at the higher doses. Open field activity also decreased by about 50%, indicating that, unlike amphetamine, compound 8739 has a tranquilizing effect rather than an activity-enhancing effect.

Many of the undesirable side effects of amphetamines were absent. Compound 8739 failed to induce "stereotypy", failed to produce an effect on "circling behavior" of striatal lesioned rats, and failed to demonstrate any adverse effects on motor function or motivation in test animals. Remarkably, there was no indication of tolerance. Failure to induce tolerance was unexpected.

Another favorable property of compound 8739 was unexpected. Previous reports have demonstrated that fatty acids, including the fatty acid of compound 8739, induce swelling of the brain. Chan, P. H., Fishman, R. A., SCIENCE, Vol. 20, 358-360 (1978). Compound 8739, however, did not induce any swelling.

The invention will no be further illustrated by the following examples.

EXAMPLE 1

A Synthesis of Compound 8739

Compound 8730 is synthesized as follows:

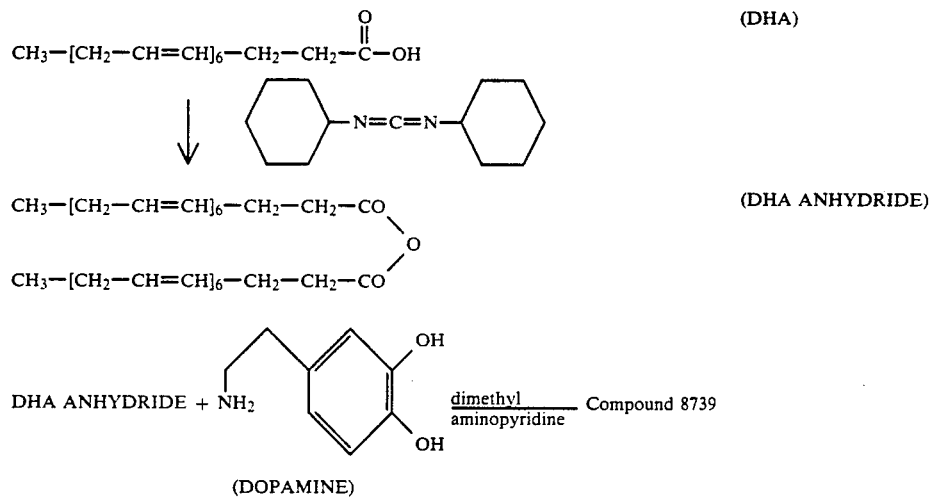

DHA is first converted to DHA anhydride in the presence of dicyclohexyl carbodiimide. This is then reacted with dopamine in the presence of 4-dimethylaminopyridine as the acid acceptor in tetrahydrofurane. In a typical experiment, 300 mg of DHA (0.009M) was dissolved in a mixture of 3 ml hexane and 4 ml benzene and stirred under nitrogen. Subsequently, a solution of 0.00615M of dicyclohexyl carbodiimide in 4 ml benzene (0.1267 g) was stirred together with the DHA for 3 hours at room temperature. A white precipitate of dicyclohexyl urea formed as the reaction proceeded. The dicyclohexyl urea was filtered off to give a clear solution of the anhydride in benzene. This solution was concentrated down to 2 ml in a rotary evaporator and diluted with 10 ml of tetrahydrofurane (dry). The freshly prepared anhydride was then added to a solution of dopamine hydrobromide (0.1053 g) (or 0.0005M) in the presence of 0.009M of 4-diethylaminopyridine (0.098 g). After stirring for thirty minutes at room temperature the initially cloudy mixture changed to a mixture of a clear liquid and a brown precipitate. At the end of the reaction, 0.2 ml of water was added to the mixture, and stirring was continued for an additional thirty minutes to completely hydrolyze any remaining unreacted anhydride. The liquid phase was isolated and evaporated to dryness to yield a brown viscous solid. This was then dissolved in a solution of 70% ethanol in water (25 ml), and the solution was then passed through a mixed-bed ion exchange resin containing a strong acidic resin based on polystyrene sulfonic acid and a strong basic resin based on quanternary ammonium substituents such as tetramethyl ammonium hydroxide (RG501, Fisher Scientific, Cambridge, Mass.) using 90% ethanol in water as the eluent. This resin removes from the mixture unreacted dopamine, dimethylaminopyridine, as well as the liberated DHA molecule. The effluent from the column (a pale yellow solution) was then evaporated in a rotary evaporator to give a solid. The product was recrystallized from aqueous ethanol (yield=75%).

The structure of compound 8739 (III) was established by mass spectrometry. The major peak (95% of the compound) consisted of a product with a mass of 550. Fragment analysis by mass spectrometry and carbon, hydrogen, infrared, and NMR spectra confirmed the structure of compound 8739.

A trimethyl silyl derivative (compound IV) of the two hydroxyl groups of dopamine was also synthesized to further confirm the structure of compound 8739. This derivative was shown to have the correct mass of 608.

two fold excess of DHA anhydride. The reaction was run overnight; the product was then evaporated to dryness and dissolved in ethanol. The compound was identified as 8739 by its migration properties on thin layer chromatography using chloroform:methanol as one solvent and dimethylformamide (DMF) as the other. The migration properties were equivalent to those of the unlabeled product.

$^{14}$C-labeled 8739 was dissolved in 15% propylene glycol in 0.1M NaHCO$_3$ and then injected subcutaneously (s.c.) into male balb C mice (20±2 g). After 5 minutes the animals were sacrificed by cervical fracture and the brain and liver were dissected out, weighed and homogenized in 8 and 10 ml of Brain Protein Solvent (BPS) buffer, respectively [BPS=2% sodium dodecyl sulfate in 0.03M Tris, 6M urea, pH 7.6, 0.01M EDTA and 0.14N NaCl]. Aliquots were then counted for $^{14}$C content in 10 ml of a liquid scintillation fluid, Liquiscent (National Diagnostic Company, Somerville, N.J.) using a Beckman liquid scintillation counter. The $^{14}$C counts were then used to calculate the total quantity of compound 8739 present in the brain per gram of tissue as compared to that in the liver. The ratio of the amount in the brain as a percent of that present in liver was determined.

RESULTS

TABLE I

Compound IV

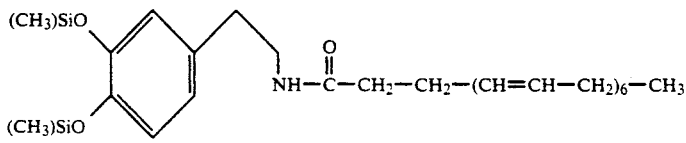

Compound 8739 was stored as a solution in ethanol (12 mg/ml) in the cold. Aliquots of this were evaporated to dryness and dissolved in 15% propylene glycol in 0.1M NaHCO$_3$ for use in biological activity tests.

EXAMPLE 2

Brain Uptake Studies

A brain penetration index (BPI) determination was used as a criterion for measuring the capacity of a compound to cross the blood brain barrier. Shashoua, V. E., Jacob, J. N., Ridge, R., Campbell, A. and Baldessarini, R. J., *J. Med. Chem.* 27, 659 (1984). The BPI is a measure of the uptake of a compound by the brain relative to its uptake by the liver. The liver is chosen as a reference since it is an organ which has no barrier of diffusable molecules present in the blood. Moreover, even if subcutaneous injections are used, the injected material tends to remain largely at the site of the injection and slowly diffuse into the circulation. Therefore, the amount of material in the liver will reflect the amount available rather than the initial dose injected.

Measurements of the quantity of the drug present in the brain and liver were measured five minutes after a subcutaneous injection and these measurements were used to calculate the BPI, the equation being:

$BPI=$[brain]/[liver]$\times 100$

For these measurements, compound 8739 was synthesized from $^{14}$C-labeled dopamine. Thirty μCi of labeled dopamine hydrochloride was mixed with 0.1 mg of unlabeled dopamine hydrobromide and reacted with a

| Compound | Brain (cpm/g) | Liver (cpm/g) | BPI Value (%) |
|---|---|---|---|
| 8739 | 1305 | 4300 | 30 |
| 8739 | 1297 | 3931 | 33 |
| Dopamine | | | 4 |
| D-glucose | | | 33 |

The results indicate that the brain uptake of compound 8739 is over eight fold higher than the brain uptake for dopamine. Compound 8739 also compares favorably with glucose which is reported in the literature to have a BPI index of 33.

EXAMPLE 3

Studies of the Pattern of Distribution of 8739 in Membranes of the Central Nervous System The utility of a drug may be determined by its ability to be taken up selectively by the particular regions of the brain upon which the drug acts. A study was made to determine the pattern of distribution of compound 8739 in the various membranes in the central nervous system. Approximately $2\times 10^6$ counts of $^{14}$C-labeled 8739 in 0.3 ml of 15% propylene glycol in 0.1M NaHCO$_3$ was injected subcutaneously into test mice (20±2 g). After thirty minutes, the animals were sacrificed by cervical fracture; the brain was then removed and homogenized in 4 ml of isotonic medium (0.14N NaCl, 0.03M Tris ph 7.4 containing 1.5 mM calcium acetate) according to the method of Whittaker (Whitaker V. P. *Biochem J.*, 72 694–706 [1959]). The fraction P1 containing nuclear and cell membrane components was sedimented for five minutes at 2,500 rpm at 0° C. The supernatant containing the crude synaptosomal fraction was next centrifuged at 13,000 rpm for thirty minutes to yield a pellet containing the curb synaptosomal fraction (P2). P1 and P2 were then dissolved in BPS, and the amount of label and protein in each fraction was determined.

RESULTS

TABLE II

| | CPM/mg Protein after Thirty Minutes of Uptake | | |
|---|---|---|---|
| Expt. No. | $P_1$ (Nuclear and Cell Membrane Fraction) | $P_2$ (Crude Synaptosomal Fraction) | $P_2/P_1$ |
| 1 | 2.7 | 5.2 | 1.9 |
| 2 | 2.7 | 5.6 | 2.1 |
| 3 | 4.19 | 12.5 | 2.9 |

As shown in Table II, the uptake of compound 8739 into the crude synaptosomal fraction (P2) was greater by a factor of an average of 2.3 than in the P1 fraction (nuclear and cell membrane fraction). This suggests that there is a preferential concentration of the compound into the synaptic fraction P2, indicating that 8739 is more highly associated with nerve endings, as would be expected from the natural distribution of DHA in lipid glycerides in such membranes.

EXAMPLE 4

Open field Motor Activity Measurement

The effect of compound 8739 on general motor activity was determined. The general motor activity of balb-c mice was measured in a Stoelting electronic activity monitor apparatus during a ninety minute period following an intraperitoneal (i.p.) injection of the compound as a solution in 15% propylene glycol in 0.1M NaHCO$_3$. A detailed description of the apparatus is reported in Stewart R. J., Campbell A., Spark G. and Baldessarini R. J. *Psychopharmacol.* 60, 281 (1979).

The test group (six mice) received an i.p. injection of the drug in a vehicle (15% propylene glycol in 0.1M NaHCO$_3$, a total volume of between about 0.1–0.3 ml). The six control mice received the same volume of vehicle, but no drug. The results (shown in FIG. 1,) are expressed as the percent decrease in open field activity for the test group versus the control group. The results indicate that compound 8739 depresses the activity of the mice by as much as 50%, demonstrating that compound 8739 is biologically active following its uptake into the brain. The response was dose dependent with higher doses of compound 8739 resulting in a greater decrease in general motor activity.

EXAMPLE 5

Figure 2:
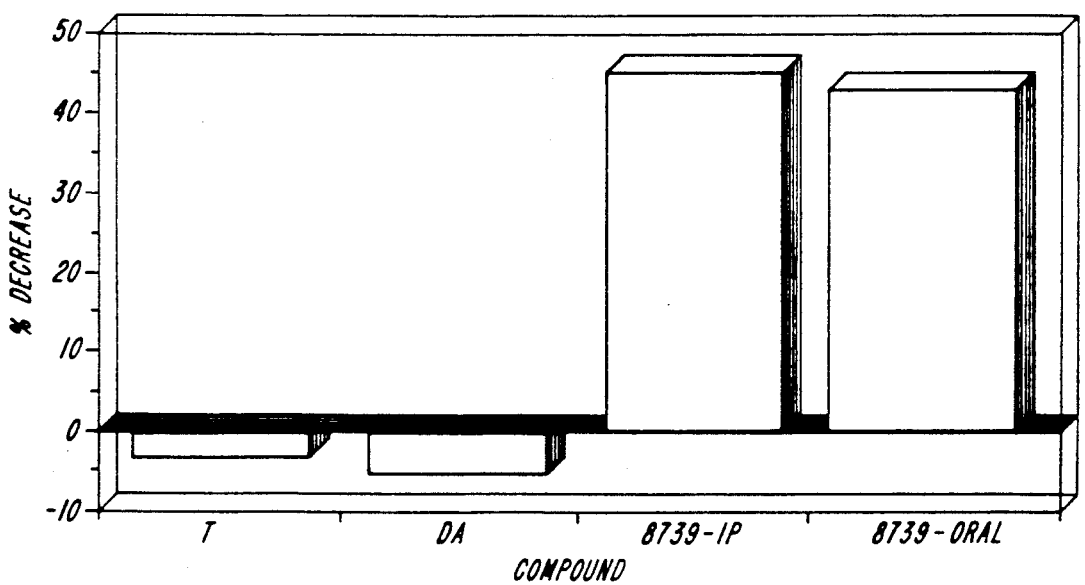
FIG. 2 is a graph comparing the effect on mice of varying the mode of delivery of the prodrug of the preferred embodiment.

Determination of the Effect of Mode of Delivery of Compound 8739 on Open Field Activity The effects of the mode of delivery of Compound 8739 (oral versus intraperitoneal injection) on the general open-field activity of mice (n=6) was assessed. As shown in FIG. 2, the drug was as active when ingested as when injected. A 40–50% decrease in activity occurred when either delivery method was employed. No significant changes in open-field activity occurred when either the carrier molecule (T) or dopamine (DA) is administered at the same dose.

EXAMPLE 6

Evaluation of Circling Behavior

Dopamine agonists such as apomorphine and compounds which release dopamine such as amphetamine cause circling behavior in animals with nigrostriatal lesions. Compound 8739 releases dopamine following proteolysis by central nervous system enzymes. It was expected that compound 8739 would cause circling behaviour in animals with nigrostriatal lesions in a manner similar to that of dopamine agonists.

Unilateral nigrostriatal lesions in rats were produced by administering unilateral injections of 6-OH dopamine into the nigrostriatum pathway. Seven days later, these animals were i.p. injected with the test drugs and circling behavior was recorded as rotations per minute during a thirty minute period in the test apparatus (Ungerstedt U. and Arbathnott G. W., *Brain Res.* 24, 485–493 [1970]).

TABLE III

| COMPOUND | DOSE (mg/kg) | AVERAGE ROTATION SCORES (Rotations/minutes) | |
|---|---|---|---|
| | | Ipsilateral | Contralateral |
| Apomorphine | 0.1 | 0.1 | 4.8 |
| " | 0.5 | 0 | 13.7 |
| Amphetamine | 3.0 | 2.5 | 0.4 |
| " | 5.0 | 3.32 | 0.92 |
| 8739 | 34 | 0.08 | 0.05 |
| " | 51 | 0.08 | 0.12 |
| Controls (uninjected) | | 0.10 | 0.12 |

Apomorphine produced a rapid circling behavior to the contralateral side of the lesion, whereas amphetamine caused circling rapidly to the ipsilateral lesion side. The enhanced contralateral rotations for apomorphine and ipsilateral rotations for amphetamine are consistent with the reported results for these dopamine agonists. Compound 8739 did not evoke this behavior. Rather, the rate of circling was very low, approximately the same as that observed for uninjected controls. Thus it appears that compound 8739 does not evoke all of the effects (side effects) of dopamine agonists.

EXAMPLE 7

Self-stimulation Data

A self-stimulation test has been used to measure the capacity of a given pharmacological agent to inhibit rats from receiving self-induced electrical stimuli via electrodes implanted in their brains (lateral hypothalamus). Stellar J. R. and Stellar E., *The Neurobiology of Motivation and Reward*, Springer-Verlag, New York, 1985. Animals will press levers to receive a pulse of current from the implanted electrode at a rate dependent upon the quantity of current that is being delivered as a reward. It is believed that the reward obtained results from the release of dopamine caused by the electrical stimulation (Stellar J. R.). The intensity of the current is varied by raising the frequency at which 250 mV pulses (0.1 msec duration) are delivered during a 0.5-sec time span. A plot of the log of the frequency of the delivered pulses vs. the rate of level press for an animal gives the self-stimulation reward curve. Injections of drugs which have a neuroleptic-type or tranquilizing effect can depress the rate of self-stimulation, shifting the response to higher current deliveries. Pimozide can give a depressed rate by about 90%. Investigations of the efficacy of compound 8739 by this test showed that the compound had no effect on either the reward or the motor aspect of the self-stimulation parameters. This indicates that compound 8739, even though it is able to cause a decrease in the general motor activity of an animal, has no effect on the motivation or the capacity to press for the "current reward". The animal continues to press the lever at the rate equivalent to a non-injected control or one receiving the vehicle alone. Thus, compound 8739 does not produce yet another effect (side effect) characteristic of postsynaptic activity of dopamine agonists.

EXAMPLE 8

Tests for Tolerance

The effect of daily i.p. injections of compound 8739 at a dose of 20 mg/kg on open field activity was tested to determine whether tolerance to the drug was induced over time. The open field activity of six test mice and six control mice was monitored for five days. Then, the test mice were given i.p. injections of the drug in a vehicle and the control mice were given i.p. injections of the vehicle only. This regimen was carried out for a twenty-one day test period. At the end of the twenty one days, the vehicle alone was given daily to both test and control mice and open field activity was monitored for an additional six days.

Figure 3:
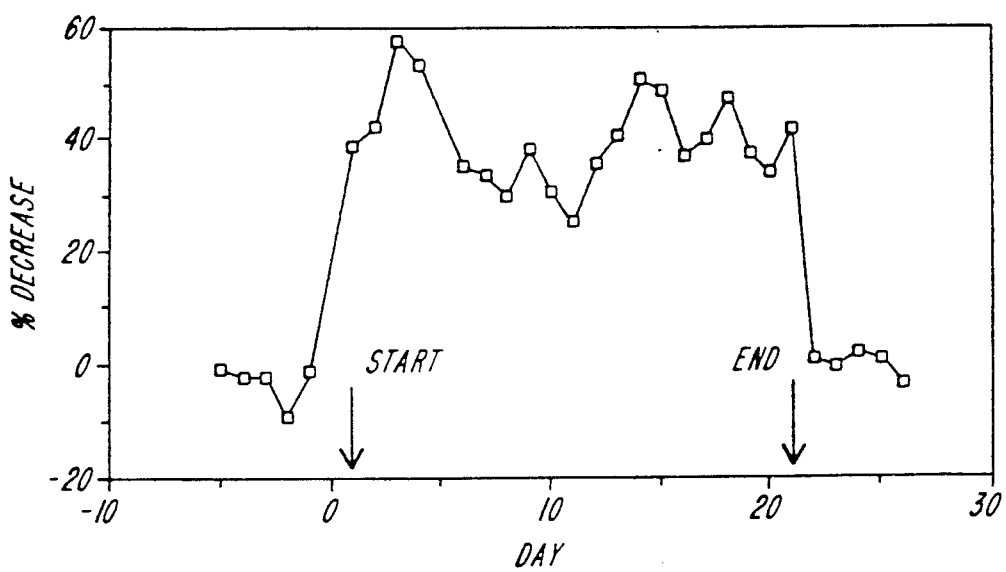
FIG. 3 is a graph showing the effect on mice of long term administration of the prodrug of the preferred embodiment.

FIG. 3 plots the percent decrease in open field activity of the test mice (n=6) as compared to the controls (n=6). As shown in FIG. 3, the level of activity prior to injections was the same for both groups. Upon initiation of injections, there was a 30% to 60% decrease in open field activity. This decrease remained fairly constant for the entire twenty-one days of injections indicating that n tolerance was induced by repeated injections during the test period. Beginning at day 22 and daily until day 27, vehicle alone was given to both groups. As shown in FIG. 3, activity returned to its predrug level when the drug administration was discontinued.

EXAMPLE 9

The Effect of Compound 8739 on Tardive Dyskinesia

An experiment was conducted to determine whether compound 8739 reduces oral dyskinesia in fluphenazine treated rats, a widely used model for human neuroleptic induced Tardive Dyskinesia (Waddington et al. *Science* 220: 530–532, 1983; Mithani et al. *Psychopharacology* 93: 94–100, 1987: et al 1987). Six adult male rats (mean weight at the start=210 g) were maintained for fifteen weeks on adlib food (available to the animal at all times) and water with fluphenazine (hereinafter FPZ) was added. The FPZ concentration in the water was 30 mg/l for eight weeks and 15 mg/l for the subsequent seven weeks. Three additional rats were maintained in similar conditions with no FPZ added to their water. During the first eight weeks, the average FPZ doses were 2.7 mg/kg/day, and for the subsequent seven weeks it was 1.2 mg/kg/day.

Each animal was tested for superfluous oral movement by placing it in a small (12×18×29 cm) transparent cage and counting non-directed oral movements for five minute periods at fifteen minute intervals. After three baseline measurement periods each animal was injected intraperitoneally either with compound 8739 (50 mg/kg) in 0.3 ml. of vehicle or 0.3 ml of vehicle (saline with 30% propylene glycol and 0.1% ascorbate).

Post injection testing started ten minutes after the injection and included three post injection test periods.

Five of the six FPZ treated animals developed significant oral dyskinesia. Counts per five minute period prior to drug or vehicle injections ranged from about 25 to 250 events. The three non-FPZ animals and one of the FPZ treated animals showed no oral dyskinesia with scores ranging from 0 to 5 events per five minute period.

Figure 4:
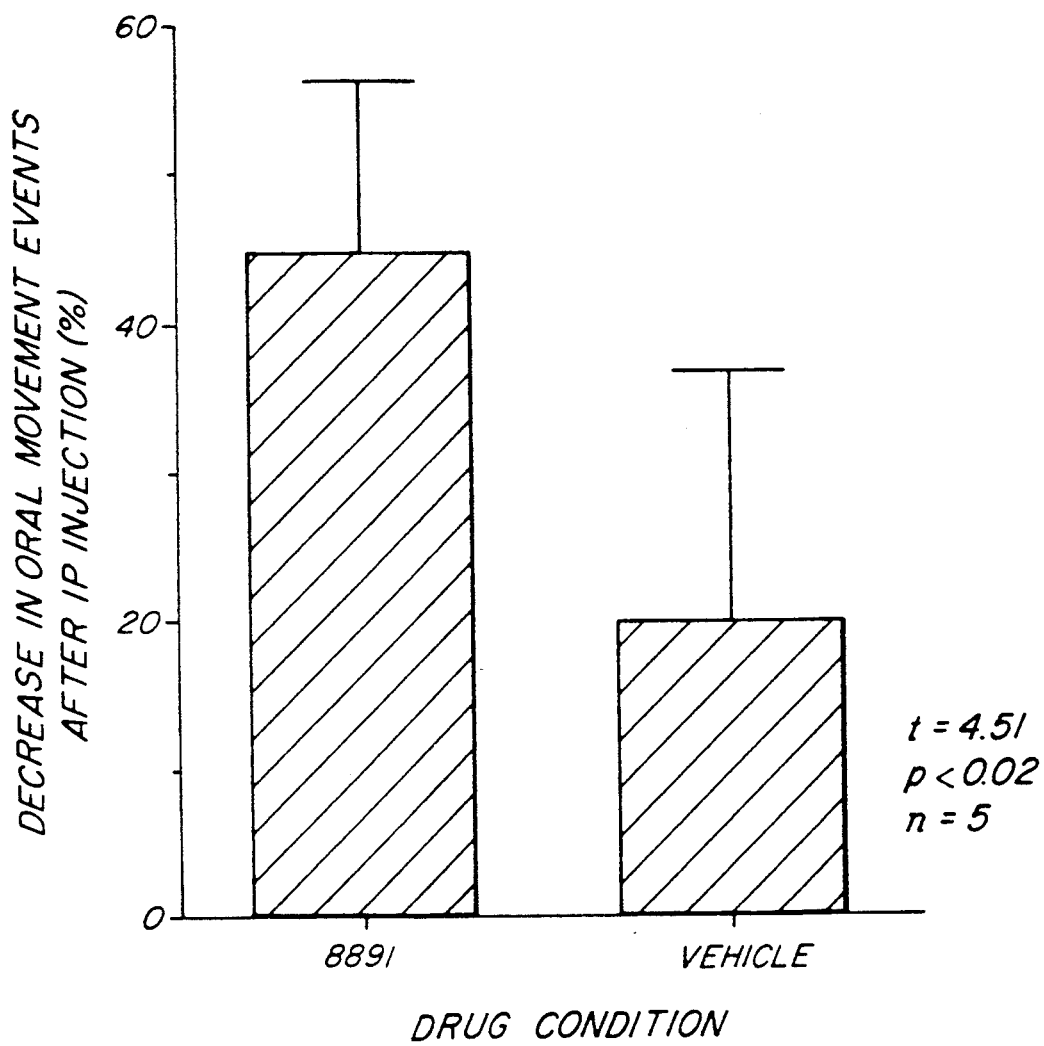
FIG. 4 is a graph showing the effect of the prodrug of the preferred embodiment on oral dyskinesia.

After injections of 8739, all five of the dyskinesic animals showed decreased oral movements as shown in Table IV and FIG. 4. The decreases for the first test period after the injection ranged from 8% to 78% (mean=44.7%+/−11.5%, N=5). Injections of vehicle only in four of five animals were also followed by a decrease in oral movements (mean=19.9%+/−16.8%, N=5).

TABLE IV

Effect of 8739 on Oral Dyskinesia in Fluophenazine Treated Rats.

| Animal Identifier | Percent change in spontaneous oral movements after injections of: | |
|---|---|---|
| | Vehicle | 8739 (50 mg/kg) |
| 1R | −27.7 | −53.2 |
| 1B | −68.5 | −77.7 |
| 2R | −27.6 | −49.3 |
| 2B | −11.6 | −35.7 |
| 2N | +36.0 | −7.6 |
| Mean | −19.9 | −44.7 |
| Standard Error Mean (SEM) | 16.8 | 11.5 |

Student's $t$ = 4.513
$p$ = .011

EQUIVALENTS

Those skilled in the art will be able to ascertain, using no more than routine experimentation, many equivalents of the specific embodiments of the invention described herein.

These and all other equivalents are intended to be encompassed by the following claims.

We claim:

1. A method for treating a subject for Tardive dyskinesia comprising,
   administering to the subject a pharmaceutically effective amount of a prodrug comprising a dopaminergic agent coupled to a fatty acid for facilitating the delivery of the dopaminergic agent across the blood brain barrier.

2. A method as claimed in claim 1 wherein the dopaminergic agent is dopamine.

3. A method as claimed in claim 1 wherein the fatty acid is a naturally occurring fatty acid.

4. A method as claimed in claim 1 wherein the prodrug comprises a fatty acid having between about 16 and about 26 carbon atoms.

5. A method as claimed in claim 1 wherein the prodrug is selected to have a BPI index of at least two times the BPI index of the dopaminergic agent.

6. A method as claimed in claim 1 wherein the prodrug administered is selected to decrease the spontaneous oral movements of the subject by at least 30 percent.

7. A method as claimed in claim 6 wherein the prodrug administered is selected to decrease the spontaneous oral movements of the subject by at least 40 percent.

8. A method as claimed in claim 1 wherein the prodrug is administered in an amount sufficient to decrease the spontaneous oral movements of the subject by at least 30 percent.

9. A method as claimed in claim 1 wherein the prodrug is administered in an amount sufficient to decrease the spontaneous oral movements of the subject by at least 40 percent.

10. A method claimed in claim 1 wherein the prodrug comprises a fatty acid coupled to the dopaminergic agent via a bond capable of being hydrolyzed in the brain.

11. A method as claimed in claim 1 wherein the fatty acid is coupled to the dopaminergic agent via an amide bond.

12. A method as claimed in claim 1 wherein the prodrug comprises a fatty acid selected from the group consisting of:

C16:0; C16:1; C16:2; C18:0; C18:1; C18:2; C18:3; C20:1; C20:2; C20:3; C20:4; C22:4; C22:5; C22:6; and C24:4 coupled to dopamine.

13. A method as claimed in claim 12 wherein the fatty acid is naturally occurring.

14. A method as claimed in claim 1 wherein a prodrug selected from the group consisting of;

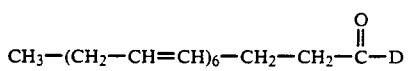

and

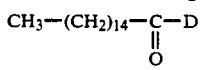

wherein D is a dopaminergic agent, is introduced into the subject.

15. A method as claimed in claim 14 wherein the dopaminergic agent is dopamine.

16. A method claimed in claim 14 wherein the prodrug

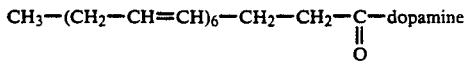

is introduced into the patient.

17. A method as claimed in claim 1, or 14 wherein the prodrug is administered with a pharmaceutically acceptable carrier.

18. A method as claimed in claim 17 wherein the prodrug administered is formulated into a capsule.

19. A method as claimed in claim 17 wherein the pharmaceutically acceptable carrier is a carrier which permits the prodrug to bypass the environment of the stomach.

20. A method as claimed in claim 17 wherein the pharmaceutical acceptable carrier is a tablet.

21. A method as claimed in claim 1 or 16 wherein the dopaminergic agent is dopamine administered in a dose between about 100 to about 20,000 micrograms per kilogram of body weight.

22. A method as claimed in claim 1 or 16 wherein the subject is a mammal.

23. A method as claimed in claim 22 wherein the subject is a human.

* * * * *